United States Patent [19]

Wang et al.

[11] Patent Number: 5,663,488
[45] Date of Patent: Sep. 2, 1997

[54] THERMAL ISOLATION SYSTEM IN AN ANALYTICAL INSTRUMENT

[75] Inventors: Tak Kui Wang, Havertown, Pa.; James W. Baker, Elkton, Md.; Terry A. Berger, Newark, Del.

[73] Assignee: Hewlett-Packard Co., Palo Alto, Calif.

[21] Appl. No.: 456,210

[22] Filed: May 31, 1995

[51] Int. Cl.[6] ........................................ G01N 7/00
[52] U.S. Cl. .............................. 73/23.25; 73/23.2
[58] Field of Search .................... 73/23.2, 23.21, 73/23.22, 23.25, 23.26, 23.23

[56] References Cited

U.S. PATENT DOCUMENTS

| | | | |
|---|---|---|---|
| 1,174,631 | 3/1916 | Snelling | 96/10 |
| 2,961,062 | 11/1960 | Hunter et al. | 183/2 |
| 3,246,764 | 4/1966 | McCormack | 210/321 |
| 3,450,196 | 6/1969 | Bauer | 165/32 |
| 3,622,303 | 11/1971 | Hill | 75/66 |
| 3,630,690 | 12/1971 | Coppola | 23/288 J |
| 3,665,680 | 5/1972 | Heuser | 55/158 |
| 3,718,434 | 2/1973 | Pierce | 23/232 R |
| 3,960,205 | 6/1976 | Laing | 165/48 |
| 4,024,036 | 5/1977 | Nakamura et al. | 204/129 |
| 4,318,828 | 3/1982 | Chapman | 252/465 |
| 4,329,157 | 5/1982 | Dobo et al. | 55/16 |
| 4,364,759 | 12/1982 | Brooks et al. | 55/487 |
| 4,474,889 | 10/1984 | Terry et al. | 436/161 |
| 4,713,234 | 12/1987 | Weerich et al. | 423/648 R |
| 4,761,164 | 8/1988 | Pez et al. | 55/16 |
| 4,886,048 | 12/1989 | Labaton et al. | 165/104.27 |
| 4,935,040 | 6/1990 | Goedert | 55/197 |
| 4,970,891 | 11/1990 | Blevins et al. | 73/19.01 |
| 5,019,517 | 5/1991 | Coulson | 436/753 |
| 5,041,265 | 8/1991 | Koike et al. | 422/94 |
| 5,105,652 | 4/1992 | Manfredi et al. | 73/23.25 |
| 5,139,975 | 8/1992 | Herron et al. | 501/7 |
| 5,141,604 | 8/1992 | Ayers | 204/59 R |
| 5,268,302 | 12/1993 | Rounbehler et al. | 436/96 |
| 5,287,725 | 2/1994 | Zhao et al. | 73/23.2 |
| 5,304,330 | 4/1994 | Tatarchuk et al. | 264/61 |
| 5,347,816 | 9/1994 | Nelson et al. | 62/46.2 |
| 5,395,990 | 3/1995 | Scarlett | 568/864 |
| 5,451,386 | 9/1995 | Collins et al. | 423/237 |
| 5,476,001 | 12/1995 | Hoetzel et al. | 73/23.31 |

(List continued on next page.)

OTHER PUBLICATIONS

Stevens, M.R., Giffin, C.E., Shoemake, G.R., and Simmonds, P.G., "A Portable Self-Contained Gas Chromatograph", The Review of Scientific Instruments, Space Sciences Division, Jet Propulsion Lab., Cal. Inst. of Tech., Pasadena, Calif., Oct. 1972, vol. 43, No. 10.

(List continued on next page.)

Primary Examiner—Hezron E. Williams
Assistant Examiner—Jay L. Politzer
Attorney, Agent, or Firm—Mark Z. Dudley

[57] ABSTRACT

Sample analysis in a portable analytical instrument, preferably in the form of a gas chromatograph, benefits from temperature control of one or more thermal zones in the instrument by way of a thermal isolation system that includes a novel pumping assembly to effect a selective amount of thermal isolation of the thermal zone. The pumping assembly includes a pumping element in the form of a tubular or planar palladium structure. The pumping assembly makes use of the unique properties of palladium to allow selective control of a nominal gas pressure within a vacuum cavity. A component system, which may include a separation column and a thermal device for heating and/or cooling the component system, may be provided within the vacuum cavity. The thermal device and the pumping assembly are individually controlled by a control system. The pumping assembly may be operated to allow selective control of the thermal isolation of the thermal zone; alternatively, the component system may be subject to a controlled temperature by operating the thermal device. A sample mixture passing through the separation column may thereby be exposed to a desired temperature profile according to a selected program so that the sample will separate into its components for subsequent detection by a detector.

18 Claims, 10 Drawing Sheets

U.S. PATENT DOCUMENTS

| | | | |
|---|---|---|---|
| 5,478,528 | 12/1995 | Golunski et al. | 422/88 |
| 5,495,747 | 3/1996 | Herman et al. | 73/23.21 |
| 5,498,278 | 3/1996 | Edlund | 96/11 |
| 5,520,538 | 5/1996 | Muka | 432/205 |
| 5,526,681 | 6/1996 | Seelby | 73/54.43 |
| 5,545,784 | 8/1996 | Weitkamp et al. | 585/250 |
| 5,569,633 | 10/1996 | Carolan et al. | 502/4 |

OTHER PUBLICATIONS

Hagiwara, Syonosuke, Shiina, Takayoshi, Takayama, Yasuo, Yano, Eiicht, "Fabrication Gas Chromatography On A Silicon Wafer", Proceedings, IECON '84, int'l Conf. on Industrial Electron, Tokyo, Oct. 22–26, 1984, IEEE, New York 1984, Inclusive Page Nos: 769–775.

Terry, Stephen C., Jerman, John H. and Angell, James B., "A Gas Chromatographic Air Analyzer Fabricated On A Silicon Wafer", IEEE Transactions on Electron Devices, Dec. 1979, vol. Ed–26, No. 12.

Lovelock, J.E., Simmonds, P.G., and Shoemake, G.R., "The Palladium Generator–Separator—A Combined Electrolytic Source and Sink for Hydrogen in Closed Circuit Gas Chromatography", Analytical Chemistry, Jet Propulsion Laboratory, Cal. Inst. of Tech., Pasadena, Cal., Aug. 1970, vol. 42, No. 9.

Lovelock, J.E., Simmonds, P.G., and Shoemake, G.R., "Gas Chromatography Using A Thermal Conductivity Detector And A Palladium Transmodulator", Analytical Chemistry, Dec. 1971, vol. 43, No. 14.

Young, J.R., "Palladium–Diaphragm Hydrogen Pump", The Review of Scientific Instruments, General Electric Research Laboratory, Schenectady, New York, Apr. 1963, vol. 34, No. 4.

Lovelock, J.E., Simmonds, P.G., Shoemake, G.R. and Rich, S., "Palladium Devices For Gas Chromatography", Journal of Chromatographic Science, Jet Propulsion Laboratory, Cal. Inst. of Tech., Pasadena, California, Aug. 1970, vol. 8.

Patapoff, Morris, "Stable Palladium Alloys For Diffusion Of Hydrogen" JPL Invention Report DO–2385/NPO–11747 from NASA Tech Brief 73–10024, Jul. 1973.

Lovelock, J.E., "Solute Switching And Detection By Synchronous Demodulation In Gas Chromatography", Journal of Chromatography, Bowerchalke, Salisbury, Wilts. (Great Britain), (1975) 29–36.

THERMAL ISOLATION SYSTEM IN AN ANALYTICAL INSTRUMENT

FIELD OF THE INVENTION

The present invention relates to methods and apparatus for the provision of a controlled thermal environment, and, more particularly, for thermal isolation of a component structure in an analytical instrument.

BACKGROUND OF THE INVENTION

Modern analytical instruments are particularly susceptible to performance variations due to the thermal sensitivity of certain components that operate within the analytical instrument. The temperature of one or more components of an analytical instrument is typically controlled by locating the component in a temperature controlled environment, or thermal zone. The temperature of the thermal zone is typically effected by an electrically-powered heating and/or cooling device.

One particular type of analytical instrument is a chromatograph. The basic components of a chromatograph include an injection port for introducing a sample of matter to be examined into a stream of carrier medium, a separation column attached to the injection port that causes some of the constituents of the sample to elute at different times, and a detector for producing a signal indicative of the presence of the constituents being eluted. An integrator may be employed for integrating the signal so as to provide information as to the quantity of each constituent.

In the typical chromatograph, the temperature controlled zone is constructed as an oven. The injection port and detector are attached to respective pneumatic fittings on the oven, and the separation column is attached between the pneumatic fittings and located within the oven. The oven typically comprises an insulated oven housing, a controlled heating element, and a stirring fan. The stirring fan continuously mixes the air contained within the oven housing so as to minimize temperature gradients therein that could adversely affect the performance of the chemical process occurring within the column. During a typical sample analysis, the heating element is operated so as to increase the temperature of the oven from a minimum initial value to a maximum final value. Before introduction of the next sample into the column, the temperature of the oven is usually returned to its initial value. With repeated use of the heating unit, fan, and other such devices, the chromatograph requires a considerable amount of power to operate.

Accordingly, a conventional chromatograph is best suited for use in the laboratory and similar settings where adequate electrical power is available. There have been attempts to reduce the size and complexity of a chromatograph so as to be practical outside of the laboratory. See, for example, Terry et al., "A Gas Chromatographic Air Analyzer Fabricated on a Silicon Wafer", IEEE Trans. Electron Devices, Dec. 1979.) Such miniaturization has not been fully realized, due in part to an unresolved need for a compact, reliable, and efficient system for providing one or more of the requisite thermal zones in the instrument.

SUMMARY OF THE INVENTION

The present invention is directed to a system for providing thermal isolation of a component system in an analytical instrument. The thermal isolation system preferably includes a housing that defines a closed cavity and a pumping assembly operatively connected to the housing for effecting a selective amount of gas pressure in the closed cavity. A component system may be subjected to temperature control in a predetermined thermal zone by positioning the component system in the closed cavity. The thermal zone may be created in the component system, or in a portion of the component system, by selective operation of a thermal device operatively connected to the component system. The thermal device may be operated to heat or cool the thermal zone. The thermal isolation may be varied by operation of the pumping assembly. Accordingly, the pumping assembly may be operated to allow selective control of the extent of thermal isolation by changing the gas pressure in the closed cavity, thereby changing the amount of heat transfer between the component system and the housing, so as to reduce the need for operation of the thermal device. As a result, the analytical instrument may be operated with greater efficiency and less power consumption. A selective change in the temperature may be effected of the component system with no operation of the thermal device, and accordingly decreases the power consumed by the analytical instrument.

In a first preferred embodiment of the invention, an analytical instrument is constructed according to the present invention to include a housing that defines a closed cavity, a pumping assembly attached to the closed cavity, a component system located in the closed cavity, a thermal device for heating or cooling the analytical assembly, and a system for controlling the operation of the pumping assembly and the thermal device.

In a second preferred embodiment of the invention, the analytical instrument may be provided as described hereinabove wherein the component system includes a gas chromatograph in a compact and reliable planar assembly that is locatable within the closed cavity. The planar assembly includes a planar member having an injection port for receiving a sample and combining the sample with a mobile phase to create a sample mixture; a separation column having a retentive media therein for effecting separation of the sample chemical mixture into at least one component; means for providing a selectable flow of the sample mixture in the separation column; and a detector for detecting the elution of the component. The thermal device is preferably integrated in the planar member and is provided in the form of a heating/cooling device that is responsive to a control signal. Also provided is a temperature sensor for sensing the temperature of the planar member and providing a temperature sense signal. The control system may be provided in the form of a computer for a) determining the current temperature of one or more of the inlet, column, and detector; b) comparing the current temperature to a desired temperature; and in response, c) providing a first control signal to the heating/cooling means and/or a second control signal to the pumping assembly for effecting a controlled temperature of one or more of the active devices in the component system.

DETAILED DESCRIPTION OF THE PREFERRED EMBODIMENTS

In one aspect of the present invention, the apparatus and methods of the present invention are directed to the provision of selective temperature control of a component system in an analytical instrument. The teachings of the present invention may also be applied to analytical instruments that may benefit from the provision of a controlled cavity pressure, such as a vacuum or a near-vacuum, in a closed cavity.

The present invention is contemplated for use in a compact and efficient analytical instrument that will find advantageous use outside of the typical laboratory setting. The teachings of the present invention may therefore be applied to both portable and laboratory-based analytical instruments, as well as to other types of instruments that may benefit from the provision of a temperature controlled thermal zone or a selectable cavity pressure.

The term "thermal zone" is meant to describe a temperature-controllable volume within which may lie an active device that is included in the component system. The term "component system" is meant to include one or more of the devices, components, subsystems, or apparatus that may form a portion of an analytical instrument. The terms "analysis" and "analytical" are meant broadly to include both qualitative and quantitative analytical methods, detection, or observation of physical or chemical parameters. For example, the apparatus and methods described herein may be applied to directly or indirectly effect selective temperature control of an element, substance, or material in the form of a "sample" that is present in, or processed by, such analysis.

Chromatographic analysis of a gaseous sample is the preferred mode of analysis according to the practice of the present invention, and the following description of the invention will be directed to an analytical instrument in the form of a compact gas chromatographic analytical system (hereinafter, a chromatograph). However, the teachings herein may be applied to analytical instruments for effecting a chromatographic analysis of liquids, multiple component gases and liquids, and mixtures thereof capable of regulated flow. Moreover, it should be understood that the teachings herein are applicable to instruments that operate using other analytical methods or that analyze or detect other physical parameters and phenomena. Mass spectrometry is one such analytical method, and a mass spectrometer represents one such alternative application.

Figure 1:
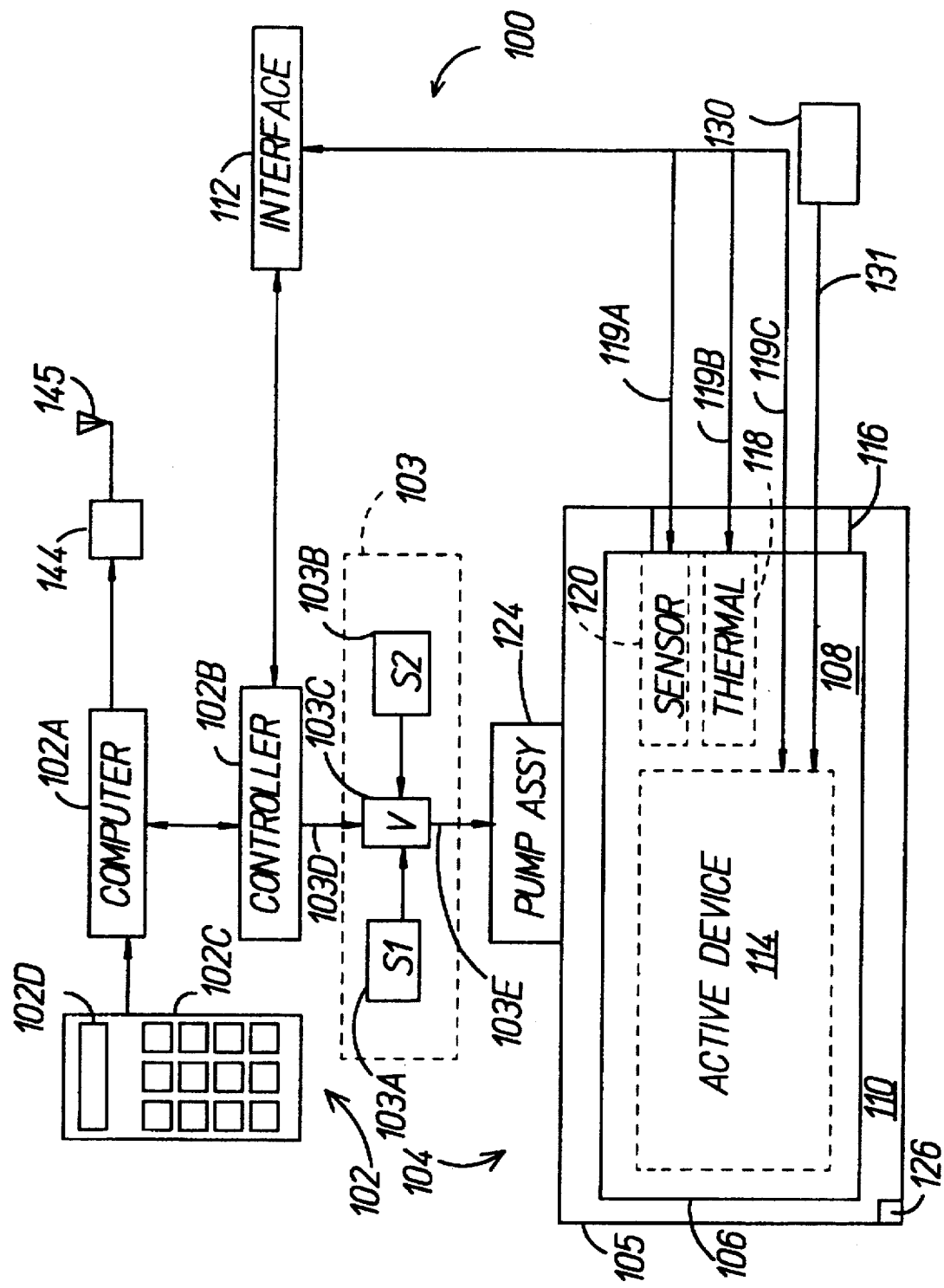
FIG. 1 is a simplified schematic representation of a novel analytical instrument constructed according to the teachings of the present invention.

Accordingly, and as illustrated in FIG. 1, one aspect of the present invention is directed to apparatus and methods to effect a selective amount of thermal isolation of a component system in an analytical instrument system 100. In particular, a control system 102, a optional gas supply system 103, and a thermal isolation system 104 may be constructed for effecting temperature control of a component system 106.

The control system 102 includes a computer 102A effecting pressure and temperature control functions through a controller 102B according to data and control algorithms stored in the computer 102A or received from an operator by way of a control panel 102C.

The thermal isolation system 104 includes a housing 105 that defines a closed cavity 110 within which is created a thermal zone 108. For the purposes of description, the closed cavity 110 will be considered as being enclosed by the housing 105; the volume defined therein will be identified as the cavity volume; and the pressure of the cavity volume (which will be seen to be selectable) will be identified as the cavity pressure. The closed cavity 110 is contemplated as being accessible from outside of the housing 105, with provision of known means (not shown), but nonetheless subject to pressurization by operation of a pumping assembly to provide a vacuum or near-vacuum within the closed cavity 110. It is a further feature of the present invention that the pressurization of the closed cavity 110 is selectable by use of the pump assembly 124 so as to allow the component system 106 to be thermally isolated to a greater or lesser extent, depending upon the gas pressure created in the closed cavity 110. In some embodiments, a check valve 126 may be provided for venting or purging gases from the closed cavity 110.

It is contemplated that a pumping assembly 124 in the form of a conventional high vacuum pump may be employed to alter the concentration of gas within the cavity volume and thereby control the transfer of heat by gas phase conduction between the component system 106 and the housing 105. Selective control of the pumping assembly 124 by a signal provided by the controller 102B directly to the pump assembly 124 can therefore provide a vacuum or near vacuum in the closed cavity. Such controlled pressurization thus effects a selected amount of thermal isolation of the component system 106. Conventional high vacuum pumps are known in the art to include diffusion pumps, turbo molecular pumps, and rotary pumps.

The gas supply system 103 is contemplated for inclusion with certain preferred embodiments of the pumping assembly 124 that compose a novel palladium pumping element, as will be described with respect to FIGS. 2A and 2B. In particular, a first gas source 103A and a second gas source 103B, the outputs of which are coupled to a valve 103C for provision of such first gas and/or second gas on a supply line 103E to the pump assembly 124. The computer 102A controls operation of the valve 103C by transmitting a drive signal on control line 103D. Selective control of the valve 103C by the controller 102B provides pressurized flow of the first or second gasses on the supply line 103E to the pump assembly 124 to thus change the cavity pressure.

The component system 106 is mounted on a thermally- and electrically-insulating connector 116. The component system 106 includes an active device 114, a thermal device provided in the form of a heating/cooling element 118, and a temperature sensor 120. The active device 114 is contemplated as being operably connected to the interface 112 by way of signal line 119C and to one or more fluid handling devices 130 by way of a respective fluid line(s) 131. Signals provided by the interface 112 on signal line 119A control the heating/cooling element 118. One or more temperature sensors 120 sense the temperature in the component system 106 and transmit a feedback signal representative of such temperature on signal line 119B to computer 102A.

The computer 102A controls the temperature of the active device 114 by one or more of the following operations with respect to the controller 102B and interface 112: (a) transmitting an appropriate signal to the pumping assembly 124 (or to valve 103C which alters the flow of the first or second gas flows), to thus respectively alter the cavity pressure; (b) transmitting a control signal to the heater/cooler element 118; and/or (c) transmitting an appropriate signal to a valve (not shown) within the heated-cooler element which alters the disbursement of a cryogenic cooling fluid. The computer 102A may thereby regulate the relative presence or absence of gas in the closed cavity 110 and accordingly the relative amount of thermal isolation of the component system 106, which thereby directly influences the temperature of the active device 114.

For the purposes of this description of FIG. 1, the active device 114 is representative of any device or component within the component system 106 that is to be operated in a thermal zone. A desired temperature in the thermal zone may be effected by the operation of the heating/cooling element 118 and/or the provision of a controlled cavity pressure in the closed cavity 110. Accordingly, in the illustrated embodiment, the thermal zone preferably encompasses at least the active device 114 but may include the entire component system 106. In other embodiments, and as will be described with respect to FIG. 2B, the contemplated thermal zone 108 may encompass a volume even greater than that occupied by the component system 106.

Various pieces of information may be entered into computer 102A by the user through the control panel 102C, and computer 102A operates to act upon the entered information or to store the entered information into a memory for later access. As such, computer 102A includes a memory in which information and programming, directed to a plurality of control functions can be stored and retrieved by known methods. Operating commands and other information, which allow selection of operating modes that cause the operating conditions of the chromatograph to change, may thus be entered into computer 102A. The control panel 102C is provided with a display screen 102D. Consequently, indicating or prompt messages can be generated by computer 102A and displayed on the display screen 102D. Computer 102A thereby maintains overall control of a plurality of functions associated with the operation of the analytical instrument system 100; in particular, it operates to control the pressurization of the closed cavity 110. Such a control function is provided by operation of the controller 102B which in turn effects control of the gas supply system 103 and an interface 112. Accordingly, the computer 102A comprises programming associated with the control of the controller 102B, gas supply system 103, heating/cooling element 118, and other systems (not shown) required for the operation of the active device 114.

Although computer 102A is shown as a single block, such computer is preferably a printed circuit board assembly that includes a central processing unit and associated peripheral devices, such as random access memories, read-only memories, input/output isolation devices, clocks, drivers, interface circuits, and other related electronic components. In the preferred embodiment, the central processor used in computer 102A is a programmable microprocessor.

The present invention also contemplates the use of various means for enhancing the versatility, portability, or miniaturization of the analytical instrument 100. For example, although computer 102A is shown as a single block, it may further comprise a network or bus system (input/output or I/O) controller, isolation devices, and other related electronic components for performing control, processing, and communication tasks other than those described herein. The computer 102A preferably includes input/output and interface ports and a low-voltage power source in the form of a battery or the like.

Computer 102A also may be operated to transfer appropriate signals to and from a telemetry section 144 and telemetry output terminal 145. The telemetry section 144 may be constructed as known in the art for transfer (transmitting and/or receiving) of information pertinent to the operation of the analytical instrument 100. Preferably, the telemetry section 144 includes a radio-frequency transceiver, an optical transceiver operating on, for example, the infrared band, or a network data interface for hardwired connection of the analytical instrument 100 to a laboratory data network or similar data transfer means (not shown). The telemetry section 144 also enhances the ability of the analytical instrument 100 to perform a particular analysis in an unattended or automatic fashion (without human intervention) in the laboratory or at a remote site.

In the preferred embodiment, the current and desired operating conditions for any given moment in time during the operation of the analytical instrument 100 are calculated by computer 102A in relation to inputted and stored information. One example of such information is a thermal zone temperature profile that may be used to influence or enhance the performance of the active device 114. Another example is information relevant to the cavity pressure in the closed cavity 110. Such information, for example, may include the current operating condition of the pump assembly 124, the state (open, closed, or proportional) of the valve 103C, the amount and state of the gas flow through the supply line 103E, and the temperature of the active device 114. For example, the actual temperature of the active device 114 and the state of the heater/cooler element 118 are known from signals received from temperature sensor 120 by the interface 112; the cavity pressure and the state of the pump assembly 124 is determined according to stored algorithms according to the composition, amount, and flow rate of the gas delivered by the valve 103C on the supply line 103E. Having calculated such operating conditions, the computer 102A can generate a variety of the requisite control signals in real time.

Figure 2A:
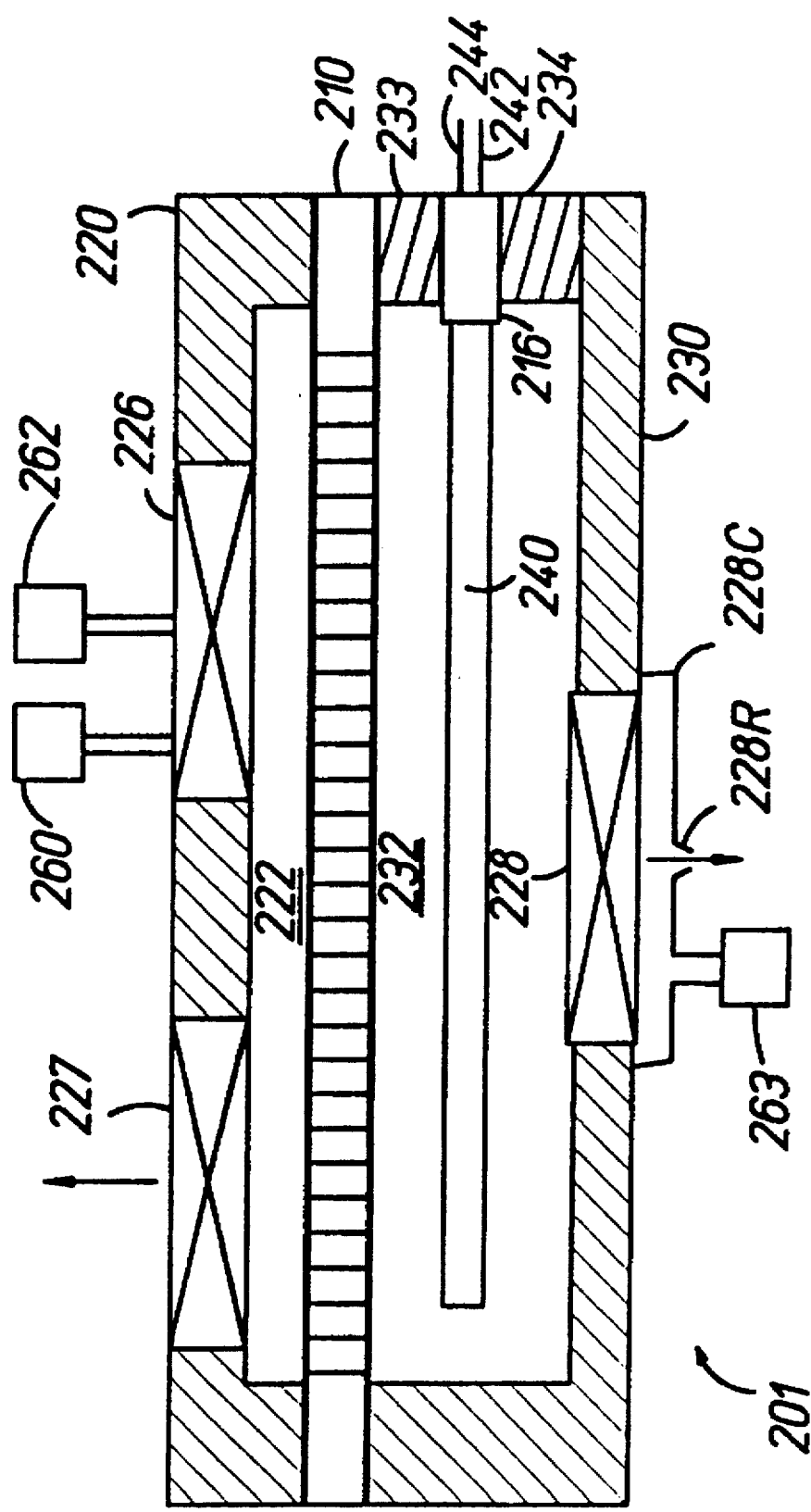
FIGS. 2A and 2B are simplified schematic representations of first and second preferred embodiments, respectively, of a thermal isolation system suitable for operation in the analytical instrument of FIG. 1.
Figure 2B:
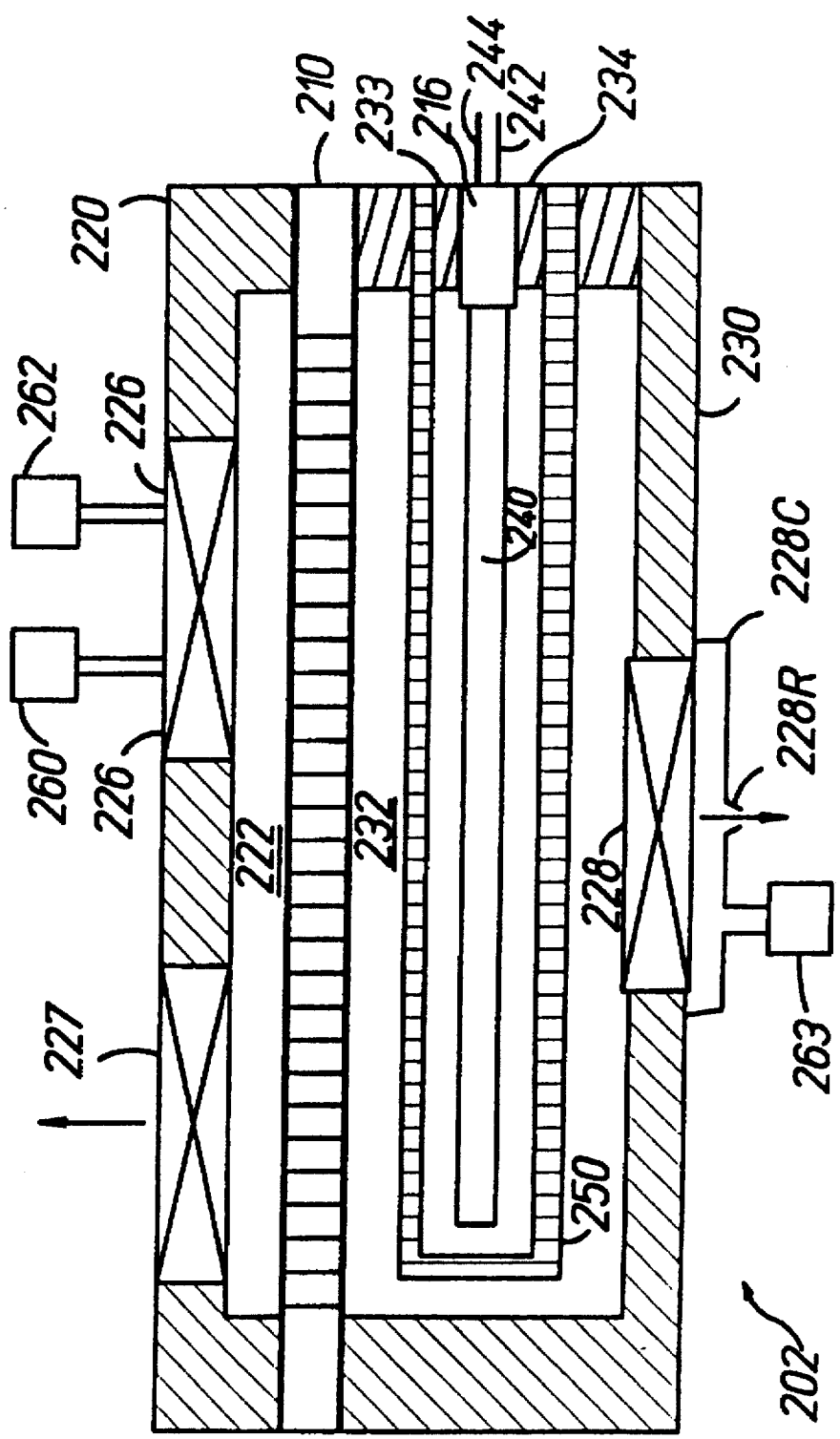

As illustrated in FIGS. 2A and 2B, the gas supply system 103 and the thermal isolation system 104 of FIG. 1 are preferably combined in a first integrated assembly 201 or in a second integrated assembly 202. With reference to FIG. 2A, the first integrated assembly 201 includes upper and lower housings 220, 230 separated by a preferred embodiment of a pumping assembly in the form of a palladium pumping element 210. The upper and lower housings 220, 230 are separable for installation or removal of the palladium pumping element 210. That is, the palladium pumping element 210 is electrically-insulated by known means and mounted between the peripheral interfaces of the upper and lower housings 220, 230; the palladium pumping element 210 is so as to a gas-tight membrane between respective upper and lower cavity volumes 222, 232. Suitable means (not shown in FIGS. 2A, 2B) are integrated within the palladium pumping element 210 so as to heat an array of palladium alloy deposits therein, as will be discussed below with respect to FIGS. 4A–4F.

The upper and lower housings 220, 230 includes first and second fluid flow regulators respectively provided in the form of a 3-way valve 226 and a relief valve 227. The lower housing 230 includes one or more connectors 216 interposed between upper and lower insulating seals 233, 234. The connector 216 is preferably formed of materials that are both thermally-insulating and electrically-insulating. The lower housing 230 also includes a third fluid flow regulator capable of allowing gas flow from the lower cavity volume 232 when a predetermined pressure is obtained in the lower cavity volume, while preventing the return flow of any gas other than hydrogen. Accordingly, the third flow regulator is provided in the form of a check valve 228 having an outlet enclosed by a hydrogen-filled cell 228C. A bleed flow of hydrogen from a hydrogen gas source 263 into the cell 228C maintains a cell vent (preferably in the form of a restrictor 228R) at a pressure slightly above ambient pressure.

A preferred embodiment of the component system 106 of FIG. 1 is provided in the form of a planar member 240 that is attached to the connector 216 so as to extend into the lower cavity volume 232. To enhance the thermal isolation of the planar member 240, it preferably is mounted in a cantilevered fashion so as to avoid contact with any structure other than the connector 216; in particular, the planar member 240 has no contact with the palladium pumping element 210 or the upper and lower housings 220, 230. A thermal zone is thus created within the majority of the planar member 240.

In the second integrated assembly 202, a gas-tight dewar envelope 250 may be provided for certain applications, such as one in which the planar member 240 is not capable of withstanding the vacuum pressures developed in the lower cavity volume 232. The thermal zone thus developed may include the planar member 240, the volume immediately surrounding the planar member 240, and a contiguous portion of the connector 216.

With respect to the internal operation of the planar member 240, the transfer of electronic signals through the connector 216 may be accomplished by use of one or more electrical feedthroughs 242; the transfer of gases and other fluid streams through the connector 216 may be accomplished by use of one or more pressurized fittings 244.

The first integrated assembly 201 and second integrated assembly 202 may be constructed in an evacuated environment such that the lower cavity volume 232 is initially at a vacuum. Alternatively, any gasses present in the lower cavity volume 232 may be purged and replaced by a predetermined concentration of hydrogen gas. In the latter instance, the computer 102A and controller 102B are operated to provide a first gas mixture that includes a partial pressure of hydrogen from a first source 260 through the 3-way valve 226 into the upper cavity volume 222. The first gas mixture, preferably under pressure, fills the upper cavity volume 222 and causes the relief valve 227 to operate at a predetermined pressure so as to purge any gases previously contained in the upper cavity volume 222. In a particular feature of the present invention, the partial pressure of hydrogen attains a sufficient concentration in the upper cavity volume 222 such that the hydrogen migrates through a plurality of palladium alloy cells distributed throughout the palladium pumping element 210 in a fashion described in greater detail below. The migration of hydrogen through the palladium pumping element 210 then displaces (purges) any gases that are present in the lower cavity volume 232 through the check valve 228. Any gases previously contained in the upper and lower cavity volumes 222, 232 are discarded, thus leaving only a selectable and equal partial pressure of hydrogen in both the upper and lower cavity volumes 222, 232. An equilibrium (i.e., the equalized partial pressures of hydrogen in the upper and lower cavity volumes 222, 232) is then achieved in the lower cavity volume, and the partial pressure in the lower cavity volume 232 attains a nominal cavity pressure.

Hydrogen gas exhibits a high coefficient of thermal conductivity. Accordingly, the desired amount of thermal isolation of the planar member 240 is then selectable by altering (increasing or decreasing) the partial pressure of hydrogen in the lower cavity volume 232. The desired amount of thermal isolation is inversely proportional to the concentration of hydrogen in the lower cavity, with the reduction limit being a vacuum or near-vacuum. For example, the desired amount of thermal isolation may be decreased by increasing the concentration of hydrogen in the lower cavity volume 232.

To reduce the hydrogen concentration in the lower cavity volume, the 3-way valve 226 is operated to allow a flow of gas other than hydrogen (such as nitrogen or oxygen) from a second gas source 262 into the upper cavity volume 222. Alternatively, the partial pressure of hydrogen in the first gas flow can be increased. The reduction of the partial pressure of hydrogen in the upper cavity volume 222 thus disturbs the equilibrium and causes a reverse migration of hydrogen gas from the lower cavity volume 232 to the upper cavity volume 222. It is a particular feature of the present invention that the reverse migration occurs through the palladium pumping element 210 via a plurality of palladium alloy cells distributed throughout the palladium pumping element 210 in a fashion described in greater detail below. A continued flow of the second gas flow can be used to reduce the partial pressure of hydrogen in the lower cavity volume to nearly zero, thus respectively creating a vacuum or a near-vacuum in the lower cavity volume 222. The second gas flow may cause the relief valve 227 to again operate at a predetermined pressure.

To increase the hydrogen concentration in the lower cavity volume, the 3-way valve 226 may be operated to increase the flow of hydrogen into the upper cavity volume 222. The flow of hydrogen increase the concentration of hydrogen in the upper cavity volume, thus again disturbing the equilibrium and causing a migration of hydrogen gas from the upper cavity volume 222 to the lower cavity volume 232. Such a flow of hydrogen can be used to alter the concentration of hydrogen in the lower cavity volume to acquire a new and desired pressure. The flow of hydrogen may cause the relief valve 227 to again operate at a predetermined pressure so as to purge a selectable amount of the second gas contained in the upper cavity volume 222. Hydrogen exhibits a high thermal conductivity and accordingly its presence in the lower cavity volume will cause gas-phase conduction of heat from the planar member to the lower housing 230. In some embodiments, the spatial separation between the planar member and the interior of the lower housing 230 can be minimized, thereby improving the desired gas-phase conduction.

When a vacuum or near-vacuum is achieved in the lower cavity volume 232, the planar member exhibits heat loss primarily by radiation from the surface of the planar member, and by conduction through the connector 216, to the surrounding structures such as the upper and lower housings 220, 230. This radiative heat loss is preferably minimized by providing a highly reflective coating on the pumping element 210 and the internal surfaces of the upper and lower housings 220, 230; conductive heat loss may be minimized by forming the connector 216 of a low thermal conductivity material. One may expect that an efficient amount of thermal isolation can be achieved at a cavity pressure in the lower cavity volume in the range of 2 Torr or less. For example, with a planar member emissivity figure of merit at 0.2 and cavity reflectivity figure of merit at 0.9, the radiative emission loss from the planar member can be considered to approximate 7% of the radiative emission loss of a blackbody source. Thus, long-term, efficient, and reliable heating and cooling of the thermal zone is feasible.

Figure 3:
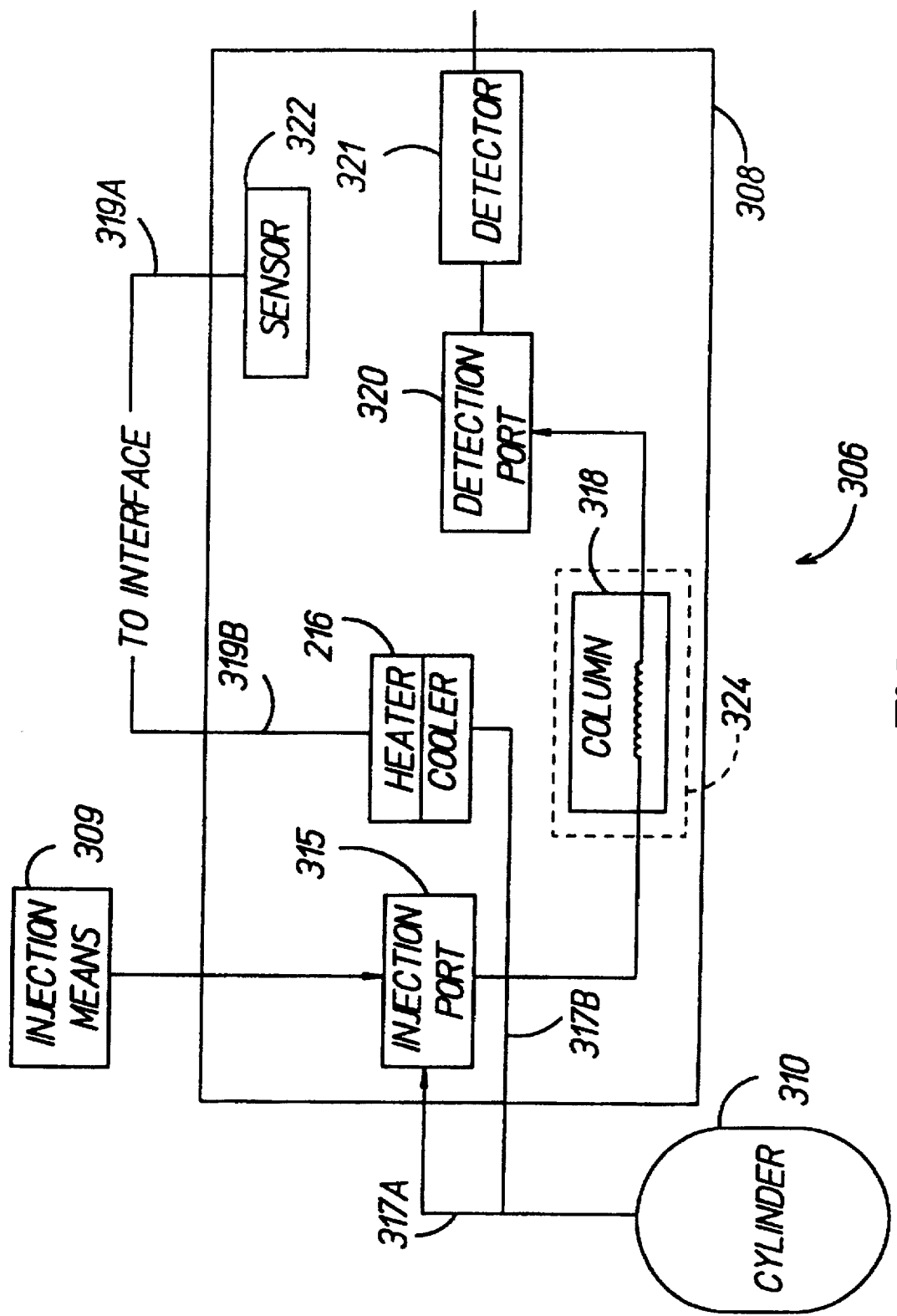
FIG. 3 is a simplified schematic representation of a component system constructed in the form of a chromatograph for operation in the analytical instrument of FIG. 1.
Figure 4:
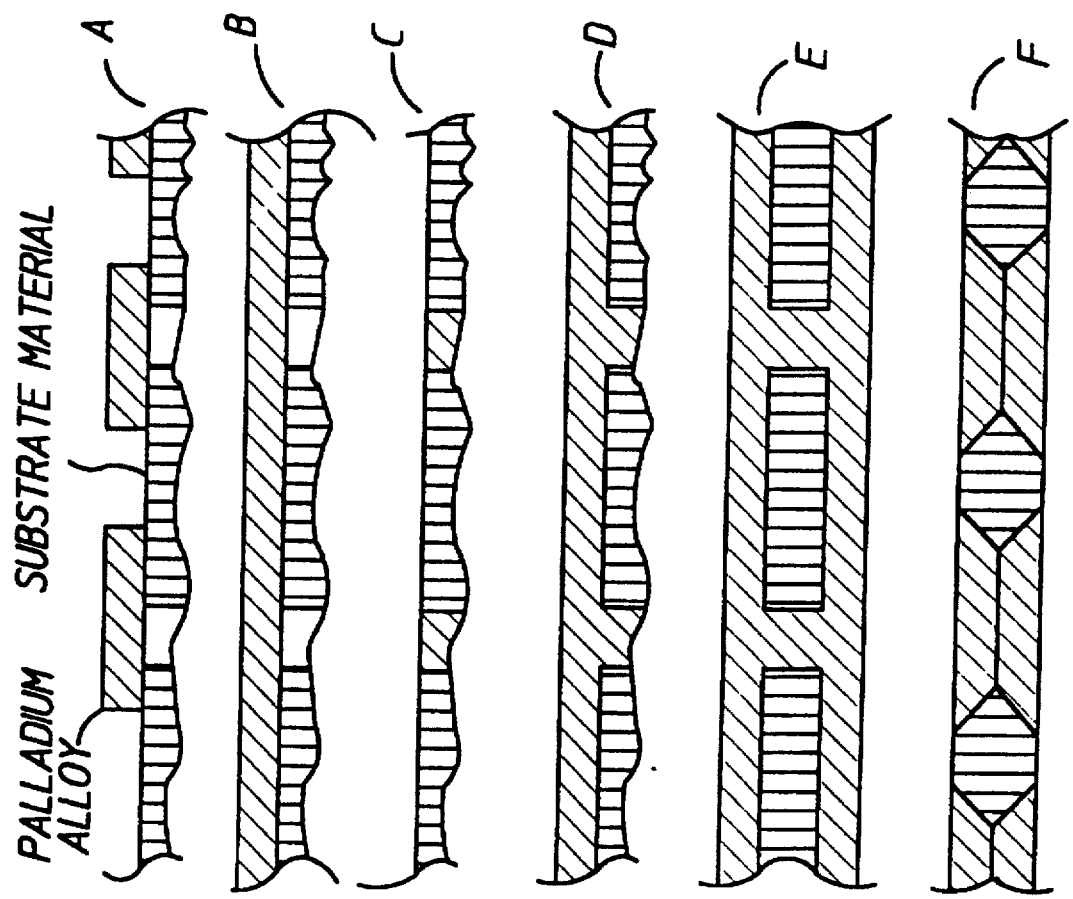
FIGS. 4A–4F are simplified side cross-sectional representations of a first preferred embodiment of a pumping element contemplated for use in the thermal isolation system of FIGS. 2A–2B.

As shown in FIG. 3, a preferred embodiment of the component system 106 is provided in the form of a miniaturized chromatograph 306 preferably constructed to perform a chromatographic analysis. The basic mechanism underlying chromatographic analysis includes the separation of a sample chemical mixture into individual components by transporting the mixture in a carrier fluid through a specially prepared separation column having a retentive media therein. The carrier fluid is referred to as the mobile phase and the retentive media is referred to as the stationary phase. A principal difference between liquid and gas chromatography is that the mobile phase is either a liquid or a gas, respectively. The present invention contemplates the use of either method, although for the purposes of simplicity, a gas chromatograph is illustrated.

In the preferred gas chromatographic analysis, a mobile phase, in the form of an inert carrier gas stream, is passed through a temperature controlled separation column that contains a stationary phase. A sample of the subject mixture is injected into the carrier gas stream and passes through the column. Separation of the sample is the result of differences in the partial pressures of each sample component in the stationary phase versus the mobile phase.

In particular, the illustrated chromatograph 306 supports programmed temperature control of a gas chromatographic analysis such that separation of the sample components is aided by differences in the volatility characteristics of each component. The present invention offers the advantage of high resolution detection of sample components in a minimal time period, because each component emerges from the outlet of the separation column at its optimum temperature. Because the highest temperature may occur at the end of a test, the present invention also offers the feature of cooling the thermal zone before beginning the next analysis. Hence, the time required between successive temperature programmed chromatographic analyses can be minimized by reducing the temperature to a desired level prior to beginning the next analysis. Such a practice can be employed to increase the number of separations performed in a given amount of time, i.e., the analytical throughput of the chromatograph 306. In addition, it is contemplated that the illustrated chromatograph 306 may be operated to provide a temperature profile having a portion below ambient temperature, particularly in an analysis of highly volatile sample components, or in an analysis conducted while the chromatograph 306 is located in an adverse (e.g., very high-temperature) ambient environment.

The basic techniques for the preparation, separation, and detection of sample components are known to those skilled in the art. The teachings herein comprehend the use of, for example, known techniques for subjecting the separation column to a specific temperature profile, and methods of controlling flow of a fluid in a chromatograph by an electronic pneumatic control system, as disclosed in Klein, et al., U.S. Pat. No. 4,994,096 and U.S. Pat. No. 5,108,466, the disclosures of which are incorporated herein by reference. See also, for example, known techniques for construction of miniaturized analytical devices, as disclosed by Terry et. al., in "A Gas Chromatographic Air Analyzer Fabricated on a Silicon Wafer", *IEEE Transactions on Electron Devices*, Vol. ED-26, No. 12, December 1979; Stevens, M. R., et. al., "A Portable Self-Contained Gas Chromatograph", in *Review of Scientific Instruments*, Volume 43, Number 10, October 1972; Hagiwara, Syonosuke, "Fabrication Gas Chromatography on a Silicon Wafer", UMI Catalog No. 13795.01, *Proc. IECON*, Oct. 22–26, 1984;, Michael, "Miniature Devices Useful for Gas Chromatography". See also U.S. Pat. No. 4,935,040; Terry, et al., "Miniature Gas Chromatograph Apparatus", U.S. Pat. No. 4,474,889, the disclosures of which is incorporated herein by reference.

With reference to FIG. 3, a sample injection means 309 is used to inject a sample into a pressurized carrier gas from a gas cylinder 310 by means of an injection port 315. (The invention also contemplates that the sample may be considered as being injected using other conventional techniques.) The carrier gas is supplied to the injection port 315 from the gas cylinder 310 via a first fluid line 317A to a fluid flow controller integrated in the injection port 315. A second pressure line 317B may be provided in certain applications as will be described below. The carrier gas may comprise one or more component gasses (e.g., hydrogen, nitrogen, or helium) depending upon the particular chromatographic separation to be performed. As known to those skilled in the art, the operation of the injection port 315 serves to control the pressure and/or the volumetric flow rate of the carrier gas into a separation column 318.

Preferably, the injection port 315, a thermoelectric heating/cooling unit 316, a separation column 318, a temperature sensor 322, a detector port 320, and a detector 321 are integrated in a chromatograph assembly 308. In the preferred embodiment, the temperature control is primarily directed to a first portion 324 that includes the separation column 318; in other embodiments, the temperature control may be implemented to encompass secondary, differing, or additional portions of the chromatograph assembly 308. Sensor 322 generates a feedback signal representative of the existing temperature in the portion 324, which signal is provided on a signal line 319A to the interface 112. The heating/cooling unit 316 may then be operated to heat and/or cool the first portion 324 in response to signals carried on signal line 319B. As a result, the carrier gas/sample combination passing through the separation column 318 is exposed to a selectable temperature profile. As the carrier gas (containing the sample) exits the separation column 318, the presence of one or more sample constituent components is detected by the detector 321.

Depending upon the application, the heater/cooler unit 316 may be constructed to perform solely as a heating device, such as a resistive heater, a thermoelectric heating and cooling device such as a Peltier device, or as a combined heater and cryogenic cooling device. For example, a desired sub-ambient temperature may be achieved through the release of a cooling fluid in the heater/cooler unit 316, whereby the cooling fluid makes a rapid transition from the liquid to the gaseous state, and then is vented away from the chromatographic assembly 308 into the ambient atmosphere. (As illustrated, the second pressure line 317B may be used to provide a quantity of the carrier gas from the carder gas cylinder 310 as the cooling fluid to the heater/cooler unit.) In the alternative, a second reservoir of cooling fluid (not shown) can be used to provide a quantity of cooling fluid on the second pressure line 317B to the heater/cooler unit.

In the preferred embodiment, the detector 321 is integrated on the chromatograph assembly 308, but in other embodiments the detector 321 may instead be external to the chromatograph 306 so as to receive the output of the detector port 320. The detector 321 can be any detector known in the art, so long as it is capable of determining at least one physicochemical property of the fluid stream which exits the separation column 318. Those skilled in the art will appreciate that the term "detector" is meant to include a wide variety of useful chromatographic detectors, such as the flame ionization detector (FID), photoionization detector (PID), nitrogen phosphorous detector (NPD), flame photometric detector (FPD), thermal conductivity detector (TCD), electrolytic conductivity detector (ELCD), and electron capture detector (ECD). The use of mass spectral detectors (MSD) and infrared spectral detectors is also contemplated. Depending upon the particular choice of detector 321, the preferred embodiments may also include means (not shown) for providing support gas to the detector 321 as known in the art.

The output signal of the detector 321 may be processed by the interface 112, controller 102B, and computer 102A for inclusion in the telemetry signal transmitted by the telemetry section 144. For example, the output of the detector 321 may be determined to cross a predetermined threshold, whereupon the computer 102A may operate the telemetry section 144 to transmit an alarm signal representative of such condition to a telemetry signal receiving and processing station (not shown). Further, the computer 102A may operate according to programmed control function, or a telemetry control signal, to effect an analysis in a discontinuous or periodic fashion, such that the chromatograph 306 is used only for brief periods. Consumption of the first and second gases, cooling fluid, carrier gas, and electrical power is thereby conserved. Any undesirable waste products may be either allowed to condense for later removal, or are vented to the atmosphere in an appropriate fashion, such as by diluting the waste output with ambient air.

FIGS. 4A–4F illustrate several planar structures suitable as a first preferred embodiment of the palladium pumping element 210 of FIGS. 2A and 2B. Each of the illustrated planar structures includes a plurality of thin-film palladium or palladium alloy deposits located in small vias (e.g., fine channels) in a planar, gas-impermeable substrate. Each of the palladium alloy deposits are preferably deposited in a thin film using known physical vapor deposition (PVD) techniques such as sputtering or electron-beam evaporation. The preferred planar structure thus comprises an array of palladium alloy cells, each of which is permeable only by hydrogen gas. The preferred composition of the substrate includes glass, ceramics, and silicon due to their low thermal conductivity. Such substrates can be metallized to become highly reflective, so as to further enhance the thermal isolation of the system component. The substrate may be prepared to incorporate the requisite array of vias by laser drilling, chemical etching, green tape cofire, or photoceramic processes.

The contemplated migration of hydrogen through the deposits may cause them to enlarge (i.e., swell). In the illustrated structures, the bulk of the substrate is expected to successfully constrain the swelling of the palladium alloy deposits in a lateral direction, that is, in a direction parallel to the major surface of the substrate. Furthermore, by using small diameter vias, the thickness of the palladium film can be minimized. As a result, the contemplated array of palladium alloy deposits will experience less compression and less tensile stress, which is a condition that is expected to be less problematic than the tensile stress experienced by conventional palladium structures.

In still another embodiment, the deposits of palladium or palladium alloy may be provided such that a predetermined, opposing tensile stress is created in the substrate to compensate for the naturally-occurring expansion that may occur during hydrogen migration. Thereafter, when subjected to hydrogen, any naturally-occurring tensile stress in the deposits is relieved. One method of creating such an opposing tensile stress may be provided by creating a difference in the thermal expansion coefficients of the substrate and the thin-film palladium alloy deposits. For example, the substrate may be chosen from those materials that exhibit a low coefficient of thermal expansion; a palladium alloy may then be deposited on the substrate after it has been heated to an elevated temperature; an opposing tensile stress will be developed in the thin-film deposits as the substrate cools.

The illustrated combination of cellular deposits in a planar structure is thus expected to exhibit greater reliability and a longer operating life than is offered in other types of structures. Further, the density, size, and thickness of the palladium alloy deposits can be selected at manufacturing to achieve an optimal (i.e., faster) migration rate of hydrogen and better control of the rate of migration by, e.g., activating only some of the elements in the array.

Further details concerning the use of palladium in a gas permeable membrane may be found in, for example, Lovelock, J. E., et. al., "Palladium Devices for Gas Chromatography", Journal of Chromatographic Science, Vol. 8, August 1970; Young, J. R., "Palladium-Diaphragm Hydrogen Pump", The Review of Scientific Instruments, Volume 34, Number 4, April 1963, "Stable Palladium Alloys for Diffusion of Hydrogen", NASA Tech Brief73-10024 from JPL Invention Report DO-2385/NPO-11747, Buttier, W. P., California Institute of Technology, Pasadena, Calif., July 1973; Labaton, et. al., "Hydrogen Pump", U.S. Pat. No. 4,886,048.

Figure 5:
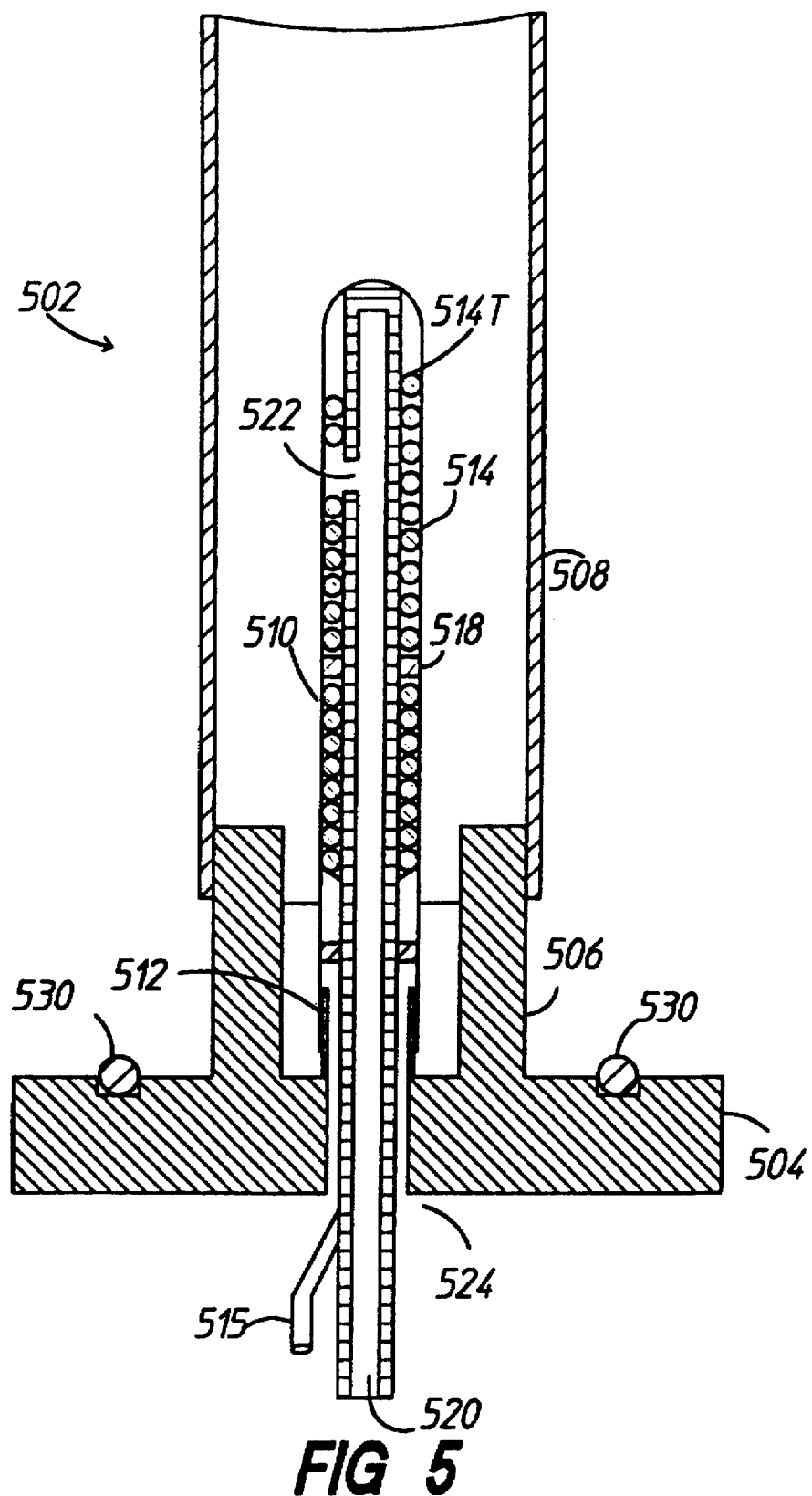
FIG. 5 is a simplified side cross-sectional representation of second preferred embodiment of a pumping element contemplated for use in the thermal isolation system of FIG. 2A–2B.
Figure 6:
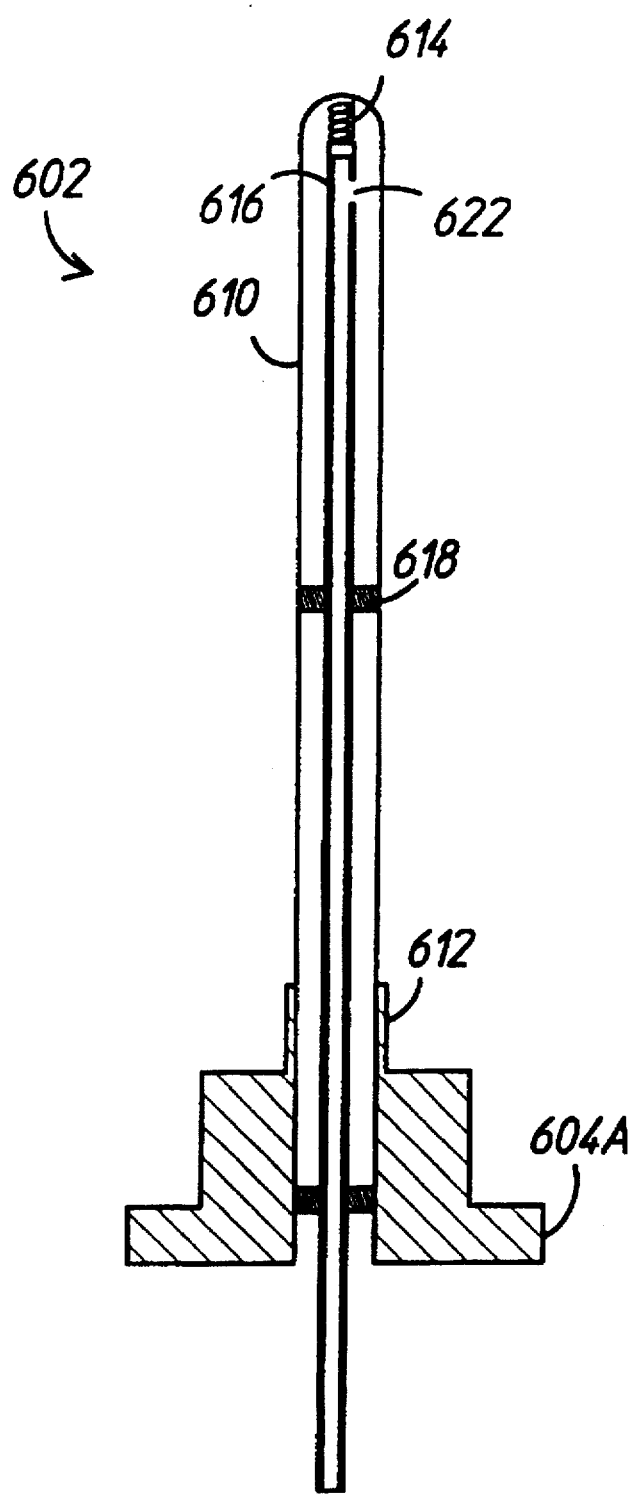
FIG. 6 is a simplified side cross-sectional representation of third preferred embodiment of a pumping element contemplated for use in the thermal isolation system of FIG. 2A–2B.
Figure 7:
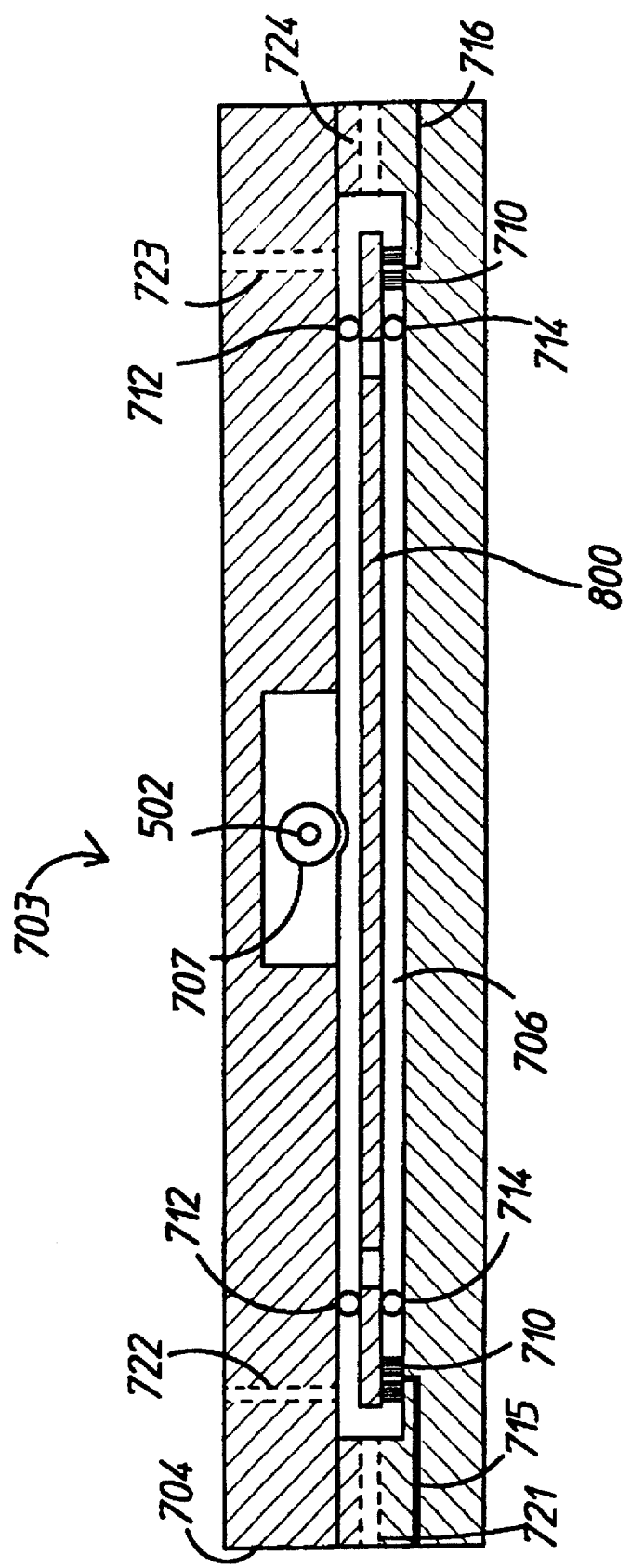
FIG. 7 is a simplified side cross-sectional representation of a third embodiment of a thermal isolation system suitable for operation in the analytical instrument of FIG. 1.

FIGS. 5 and 6 respectively illustrate second and third preferred embodiments, respectively, of a palladium pumping element for use in a thermal isolation system constructed as a third integrated assembly 703, as illustrated in FIG. 7. The second preferred embodiment 502 may be constructed as having a base 504, a shield support 506, a heat shield 508, a palladium alloy thimble 510, a thimble support 512, and a resistive heating element in the form of a cartridge heater 514. Most of the second preferred embodiment 502 may be situated in a closed cavity 706 after the base 504 is clamped by known means (not shown) into a bore 707 in the wall of the third integrated assembly 703. The base 504 accommodates a compressible sealing ring 530 so as to provide a gas-tight seal. The cartridge heater 514 and a flow tube 516 are concentric within the palladium alloy thimble 510 by use of perforated spacers 518. The cartridge heater 514 is supplied with electrical current by use of a lead 515. The flow tube 516 and lead 517 extend through a central bore 517 in the base 504. Electrical current may be selectively applied on the lead 515 from an appropriate source (such as the interface 112 of FIG. 1) to causes the cartridge heater 514 to heat the flow tube 516 and the palladium alloy thimble 510. The flow tube 516 includes an inlet 520 and an outlet 522 such that gas flow supplied to the inlet 520 will pass through the flow tube 516, become pre-heated, and exit the outlet 522. The heated gas flow then proceeds along the interior wall of the heated palladium alloy thimble 510 and through the perforated spacers 518 before exiting the central aperture 524.

The third preferred embodiment 602 is structurally similar to the second preferred embodiment 502 but omits the resistive heater coil 514 and heat shield 508. The flow tube 616 and/or the palladium alloy thimble 610 may be resistively heated by an electrical current supplied by known connector means (not shown). Electrical current may be provided to the exposed end of the flow tube 616 and returned to the current source by conduction through the sidewall of the flow tube 516, a coiled contact 614 attached to the outlet end of the flow tube 616, and the sidewall of the thimble 610 to the base 604, which is connected by known means (not shown) to an electrical ground. For example, the sidewalls of the thimble 610 may be very thin and thus resistive to current flow.

Figure 9:
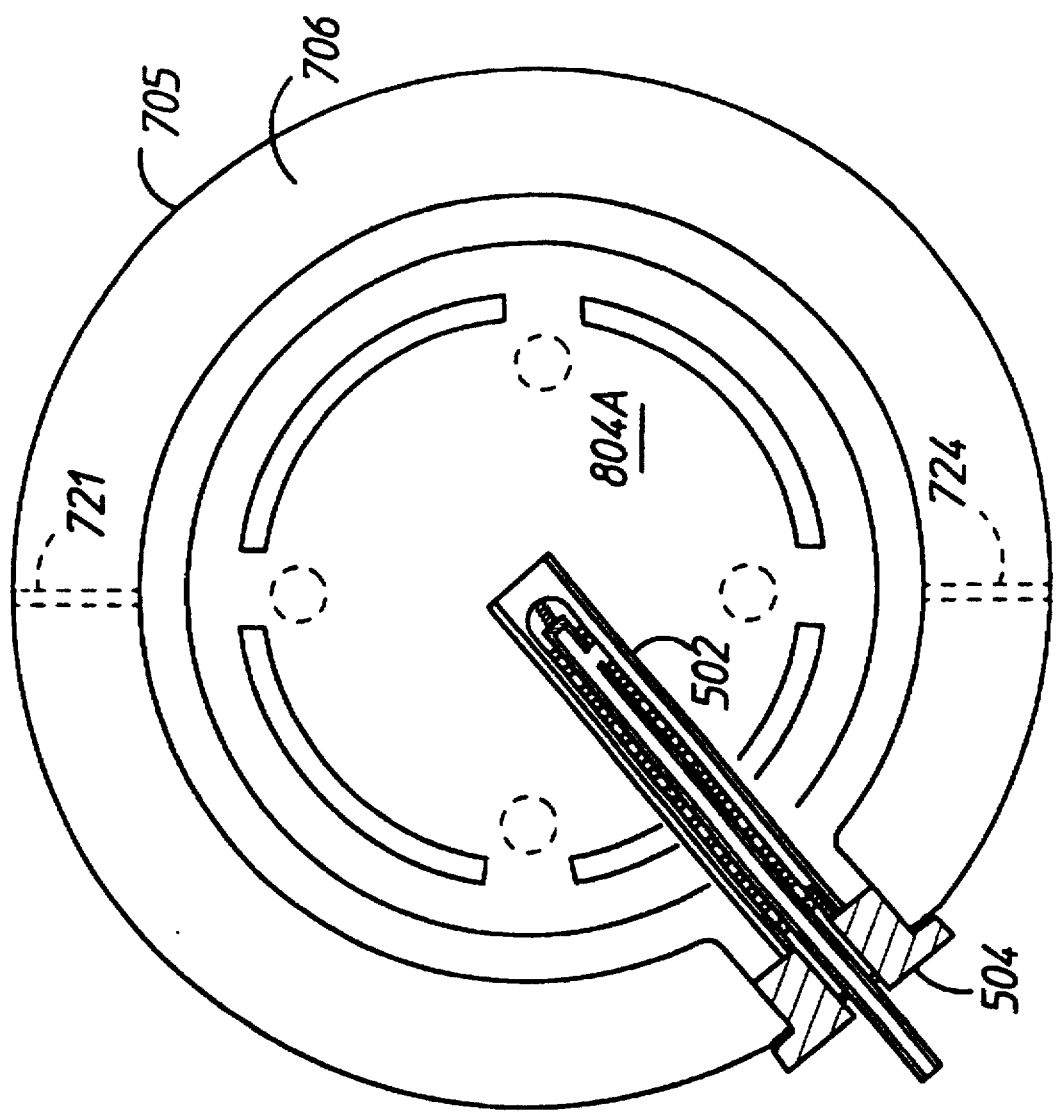
FIG. 9 is a top plan view of a the thermal isolation system of FIG. 7.

FIGS. 7 and 9 illustrate a third embodiment Of a thermal isolation system in the form of a third integrated assembly 703 having an upper housing 704 and a lower housing 705 which, when clamped together, define a closed cavity 706. Positionable in the closed cavity 706 is a preferred embodiment of the miniaturized gas chromatographic system 306 of FIG. 3 that is provided in the form of a unitary, multilayer, planar assembly 800. Insulating connector blocks 710, an upper seal ring 712, and a lower seal ring 714 position the planar assembly 800 within the cavity 706 so as to avoid contact with the upper and lower housings 704, 705. Electrical signals and fluid flows may be provided to the assembly by use of feedthroughs 715 and fluid paths 716 that are integral to the lower housing 705. Additional access to the planar assembly 800 by, for example, a slender conduit in the form of an injection syringe needle, a probe, or the like may be provided by way of lateral access bores 721,724 and vertical access bores 722, 723. Each of the feedthroughs, fluid paths 716, and access bores 721-724, are preferably fitted with pressure seals (not shown) such as glands or suitable surface fittings so as to allow the closed cavity 706 to be pressurized.

Figure 8:
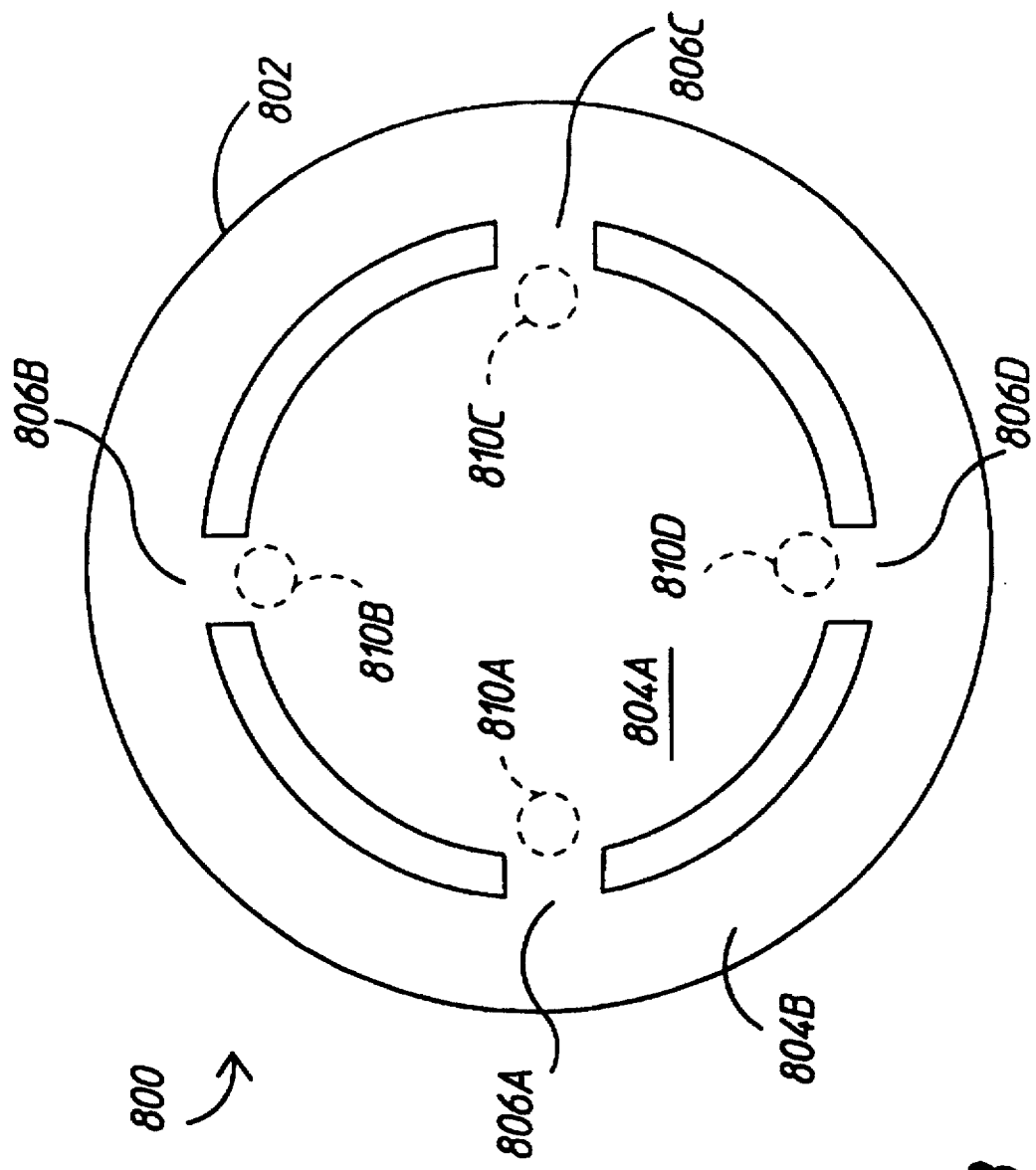
FIG. 8 is a top plan view of a planar chromatographic device suitable for use in the thermal isolation system of FIG. 7.

FIG. 8 illustrates the planar assembly 800 in plan view and FIG. 9 illustrates the planar assembly 800 as it is positioned within the lower housing 705 before attaching the upper housing 704. The body 802 of the planar assembly 800 is constructed according to multiple layer micromachining fabrication techniques, and includes an inner portion 804A, subject to thermal isolation as described hereinabove, and an outer circumferential portion 804B. The inner portion 804A is supported on the circumferential portion 804B by radial legs 806A-806D. The outer circumferential portion 804B is sized and shaped so as to engage the connector blocks 710 and be compressed between the lower seal ring 714 and the upper seal ring 712 when the upper housing 704 is clamped to the lower housing 705. The inner portion 804A is then supported within the closed cavity 706 by the radial legs 806A-806D.

The inner portion 804A includes an integral distributed heater layer preferably in the form of a thin-film platinum layer to provide a uniform distribution of heat in the inner portion 804A and to lower radiative heat loss. Conductive heat transfer between the inner and circumferential portions 804A, 804B is minimized by reducing the cross-section of the radial legs 806A-806D and by the provision of individual heating/cooling elements 810A-810D within the inner portion 804A and respectively adjacent the radial legs 806A-806D. Appropriate thin-film temperature sensors located in the inner portion 804A and the elements 810A-810D provide temperature feedback signals as needed.

Those skilled in the art will appreciate that numerous changes and modifications may be made to the preferred embodiments of the invention and that such changes and modifications may be made without departing from the spirit of the invention. For example, while the disclosed embodiments of the present invention have been described as being fabricated from a silicon substrate, other materials such as metal, glass, ceramic, or polymers, and other semiconductor or crystalline substrates may also be used. For example, the planar structures described herein may be fabricated according to one or more of the following alternatives: borosilicate glass may be fabricated using ultrasonic machining; photosensitive glass may be formed by lithography; a ceramic material may be ultrasonically machined, injection molded, or cast and fired; a metal or machinable ceramic may be formed by conventional machining; or a polymer may be machined, cast, or injection molded.

What is claimed is:

1. Apparatus for providing thermal isolation of a component system in an analytical instrument, comprising:

a housing defining a closed cavity and a cavity volume, said closed cavity being subject to pressurization and thereby having a cavity pressure;

means for locating the component system and the housing in a spaced relationship wherein at least a portion of said component system is enclosed within and detached from said housing; p1 a pumping assembly having a palladium pumping element operatively connected to the cavity for controlling cavity pressure in response to a pressure control signal; and a controller operatively connected to the pumping assembly for providing said pressure control signal; wherein said controller includes means for determining a selected cavity pressure and means for providing said pressure control signal in response to said determination so as to control the cavity pressure in the closed cavity, whereby the extent of gas phase heat conduction between said portion of the component system and the housing is selectably controlled.

2. The apparatus of claim 1, further comprising a thermal device operatively connected to the component system and responsive to a thermal control signal for effecting a thermal zone in said portion of the component system.

3. The apparatus of claim 2 wherein the thermal device further comprises a thermoelectric device.

4. The apparatus of claim 2, wherein said pumping assembly further comprises a gas supply system for providing a first flow of hydrogen gas in response to said pressure control signal and a palladium pumping element located with respect to said closed cavity and being responsive to the provision of the first flow for controlling the cavity pressure in the cavity volume.

5. The apparatus of claim 4, wherein the gas supply further comprises means for providing a second flow of gas other than hydrogen, and wherein said first and second flows are provided in response to said pressure control signal for controlling the selectable cavity pressure in the cavity volume.

6. The apparatus of claim 5, wherein the pumping element is provided in the form of a tubular palladium structure.

7. The apparatus of claim 5, wherein the pumping element is provided in the form of a planar palladium structure.

8. The apparatus of claim 4, further comprising:

an active device that is operatively connected to the thermal device;

a temperature sensor for sensing a temperature of the active device and providing a temperature sense signal to said controller;

wherein said controller includes means for determining the current temperature of the active device from the sense signal, comparing the current temperature to a desired temperature, and in response, providing pressure control signal.

9. The apparatus of claim 8, wherein the active device, thermal device, and temperature sensor are integrated in the form of a planar assembly located within the closed cavity.

10. The apparatus of claim 9, wherein the planar assembly further comprises a a gas chromatograph integrated in the planar assembly.

11. The apparatus of claim 9, wherein gas chromatograph is constructed in the form of a planar member and the active device is selected from a group including: an injection port for receiving a sample and combining the sample with a mobile phase to create a sample mixture; a separation column having a retentive media therein for effecting separation of a sample chemical mixture into at least one component; means for providing a selectable flow of a sample mixture in a separation column; and a detector for detecting the elution of a sample component.

12. An analytical instrument, comprising:
- a component system having an active device and a thermal device for altering the temperature of the active device;
- a thermal isolation system for receiving the component system and providing temperature control of a thermal zone, said active device being located in the thermal zone, including:
  - a. a housing defining a closed cavity and a cavity volume, said closed cavity being subject to pressurization and thereby having a cavity pressure, said housing including means for locating the component system and the housing in a spaced relationship wherein at least a portion of said component system is enclosed within and detached from said housing,
  - b. a gas supply system responsive to a control signal for providing a first flow of hydrogen gas,
  - c. a pumping assembly having a palladium pumping element located with respect to said closed cavity and operable in response to the provision of first flow for establishing a selectable cavity pressure in the cavity volume and thereby establishing a selected amount of thermal isolation of the thermal zone; and
  - d. a controller operatively connected to the pumping assembly for providing said pressure control signal; wherein said controller includes means for determining a selected cavity pressure and means for providing said pressure control signal in response to said determination so as to control the cavity pressure in the closed cavity, whereby the extent of gas phase heat conduction between said portion of the component system and the housing is selectably controlled.

13. The analytical instrument of claim 12, wherein the controller further comprises a memory device for storage and retrieval of a program for effecting a temperature profile.

14. The analytical instrument of claim 12, wherein the controller further comprises an information input device for receiving information representative of a temperature profile.

15. The analytical instrument of claim 12, wherein the controller further comprises a telemetry section for communication of information representative of a temperature profile.

16. The analytical instrument of claim 12, wherein the active device further comprises:
- an injection port for receiving a sample and combining the sample with a mobile phase to create a sample mixture;
- a separation column having a retentive media therein for effecting separation of the sample mixture into at least one component;
- means for providing a selectable flow of the sample mixture in the separation column; and
- a detector for detecting the component.

17. A method for providing thermal isolation of a component system in an analytical instrument, comprising the steps of:
- providing a control system for supplying at least one of a first and a second control signals;
- providing a housing defining a closed cavity and a cavity volume, said closed cavity being constructed to accommodate at least a portion of the component system, the closed cavity being subject to pressurization and thereby having a cavity pressure;
- locating the component system and the housing in a spaced relationship wherein the portion of said component system is enclosed within and detached from said housing;
- operatively connecting a thermal device to the component system and operating the thermal device in response to the first control signal for effecting a thermal zone in the portion of the component system; and
- operatively connecting a pumping assembly having a palladium pumping element to the housing and operating the pumping assembly in response to the second control signal for effecting a selective amount of cavity pressure in the closed cavity, whereby the extent of gas phase heat conduction between the portion of the component system and the housing is selectably controlled.

18. An analytical instrument, comprising:
- a component system having an active device and a thermal device for altering the temperature of the active device;
- a thermal isolation system for receiving the component system and providing temperature control of a thermal zone, said active device being located in the thermal zone, including:
  - a. a housing defining a closed cavity and a cavity volume, said closed cavity being subject to pressurization and thereby having a cavity pressure, said housing including means for locating the component system and the housing in a spaced relationship wherein at least a portion of said component system is enclosed within and detached from said housing,
  - b. a gas supply system responsive to a control signal for providing a first flow of hydrogen gas,
  - c. a pumping assembly having a palladium pumping element located with respect to said closed cavity and operable in response to the provision of first flow for establishing a selectable cavity pressure in the cavity volume and thereby establishing a selected amount of thermal isolation of the thermal zone;
  - d. a controller operatively connected to the pumping assembly for providing said pressure control signal; wherein said controller includes means for determining a selected cavity pressure and means for providing said pressure control signal in response to said determination so as to control the cavity pressure in the closed cavity, whereby the extent of gas phase heat conduction between said portion of the component system and the housing is selectably controlled; and
- a telemetry section for communication of information representative of a temperature profile.

* * * * *

UNITED STATES PATENT AND TRADEMARK OFFICE
CERTIFICATE OF CORRECTION

PATENT NO.  : 5,663,488
DATED       : September 2, 1997
INVENTOR(S) : T. K. Wang et al.

It is certified that error appears in the above-indentified patent and that said Letters Patent is hereby corrected as shown below:

Claim 1, line 9, delete " $p^1$ "

Signed and Sealed this

Twenty-eighth Day of December, 1999

Attest:

Q. TODD DICKINSON

*Attesting Officer*  *Acting Commissioner of Patents and Trademarks*